(12) United States Patent
Sano et al.

(10) Patent No.: US 10,729,398 B2
(45) Date of Patent: Aug. 4, 2020

(54) RADIATION PHASE CONTRAST IMAGING DEVICE

(71) Applicants: Shimadzu Corporation, Kyoto (JP); OSAKA UNIVERSITY, Suita-shi (JP)

(72) Inventors: Satoshi Sano, Kyoto (JP); Koichi Tanabe, Kyoto (JP); Toshinori Yoshimuta, Kyoto (JP); Kenji Kimura, Kyoto (JP); Hiroyuki Kishihara, Kyoto (JP); Yukihisa Wada, Kyoto (JP); Takuro Izumi, Kyoto (JP); Taro Shirai, Kyoto (JP); Takahiro Doki, Kyoto (JP); Akira Horiba, Kyoto (JP); Takayoshi Shimura, Suita (JP); Heiji Watanabe, Suita (JP); Takuji Hosoi, Suita (JP)

(73) Assignees: Shimadzu Corporation, Nishinokyo-Kuwabaracho, Nakagyo-ku, Kyoto-shi, Kyoto (JP); Osaka University, Yamadaoka, Suita-shi, Osaka (JP)

( * ) Notice: Subject to any disclaimer, the term of this patent is extended or adjusted under 35 U.S.C. 154(b) by 0 days.

(21) Appl. No.: 16/335,210

(22) PCT Filed: Jul. 28, 2017

(86) PCT No.: PCT/JP2017/027566
§ 371 (c)(1),
(2) Date: Mar. 20, 2019

(87) PCT Pub. No.: WO2018/061456
PCT Pub. Date: Apr. 5, 2018

(65) Prior Publication Data
US 2019/0343472 A1 Nov. 14, 2019

(51) Int. Cl.
*A61B 6/00* (2006.01)
*A61B 6/08* (2006.01)

(52) U.S. Cl.
CPC ............ *A61B 6/484* (2013.01); *A61B 6/4291* (2013.01); *A61B 6/08* (2013.01); *A61B 6/4035* (2013.01)

(58) Field of Classification Search
CPC ......... A61B 6/484; A61B 6/4291; A61B 6/08; A61B 6/4035
(Continued)

(56) References Cited

U.S. PATENT DOCUMENTS

| 8,243,879 B2 * | 8/2012 | Itoh | ................... G21K 1/025 |
| | | | 359/238 |
| 2012/0020454 A1 | 1/2012 | Murakoshi | |

FOREIGN PATENT DOCUMENTS

| JP | 2012-016370 A | 1/2012 |
| JP | 2012-024339 A | 2/2012 |

OTHER PUBLICATIONS

International Search Report dated Sep. 19, 2017 for PCT application No. PCT/JP2017/027566.
(Continued)

*Primary Examiner* — Courtney D Thomas
(74) *Attorney, Agent, or Firm* — Muir Patent Law, PLLC

(57) ABSTRACT

An X-ray phase contrast imaging device of the present invention can change an arrangement pitch of slits related to a multi-slit and an arrangement pitch of phase shift sections related to a phase grating. A positional relationship among the multi-slit 3b, the phase grating, and an FPD is determined based on the arrangement pitch of the slits related to the multi-slit, the arrangement pitch of the phase shift sections related to the phase grating, and an arrangement pitch of detection elements related to the FPD. Among these
(Continued)

arrangement pitches, by changing the arrangement pitch of the slits and the arrangement pitch of the phase shift sections, the present invention can change the positional relationship among the multi-slit, the phase grating, and the FPD.

7 Claims, 10 Drawing Sheets

(58) Field of Classification Search
USPC .......................................................... 378/62
See application file for complete search history.

(56) References Cited

OTHER PUBLICATIONS

Written Opinion of the ISA dated Sep. 19, 2017 for PCT application No. PCT/JP2017/027566.

* cited by examiner

SWITCHING OPERATION

RADIATION PHASE CONTRAST IMAGING DEVICE

TECHNICAL FIELD

The present invention relates to a radiation phase contrast imaging device that images an internal structure of an object by using a phase contrast of a radiation that is transmitted through the object.

BACKGROUND ART

Conventionally, various radiation imaging devices that cause an object to transmit a radiation and images an internal structure of the object are devised. A general radiation imaging device captures a projection image of a radiation by applying the radiation to an object and causing the object to transmit the radiation. A variation in density appears in such a projection image in proportion to a radiation transmission level and represents an internal structure of the object.

Such a radiation imaging device can capture an image of only an object having characteristics of absorbing a radiation to some extent. For example, a biological soft tissue may absorb almost no radiation, or may have almost no absorption difference from surrounding substances. Even if a general device captures an image of such a tissue, almost nothing will be reflected in the projection image. Thus, imaging an internal structure of an object having no radiation absorption difference with a general radiation imaging device is theoretically limited.

Therefore, a radiation phase contrast imaging device that images an internal structure of an object by using a phase change of a transmitted radiation has been devised. Such a device images an internal structure of an object by using Talbot interference (for example, refer to Patent Literature 1).

FIG. 21 describes a radiation phase contrast imaging device. The radiation phase contrast imaging device includes a radiation source 53a that emits a radiation, a multi-slit 53b that makes a phase of the radiation uniform, a phase grating 55 having a bamboo blind-shaped pattern, and a detector that detects the radiation. The device of FIG. 21 has a configuration in which a subject is placed at a position sandwiched between the phase grating 55 and the detector. The multi-slit 53b has a configuration in which slits extending vertically are arranged laterally. The phase grating 55 has a configuration in which longitudinally extending shielding wires that do not easily transmit the radiation are arranged laterally.

A principle of the radiation phase contrast imaging device will be briefly described. When a radiation is emitted to the phase grating 55, a self-image of the phase grating 55 appears at a position distant from the phase grating 55 by a specified distance (Talbot distance). A position of the detector with respect to the phase grating 55 is adjusted such that this self-image is reflected. This self-image is an image that looks like a shadow of the phase grating 55 reflected. However, it is to be noted that the self-image is an interference fringe generated by radiation interference, and is not a mere projection.

When the subject is installed between the phase grating 55 and the detector, the radiation emitted from the phase grating 55 is transmitted through the subject before being detected by the detector. The self-image that appears on the detector at this time is slightly disturbed by being transmitted through the subject. This disturbance results from a phase shift while the radiation is transmitted through the subject.

CITATION LIST

Patent Literature

Patent Literature 1: JP 2012-24339 A

SUMMARY OF INVENTION

Technical Problem

However, the radiation phase contrast imaging device of a conventional configuration has the following problem.

That is, the radiation phase contrast imaging device of a conventional configuration has a problem of lacking flexibility in imaging.

The radiation phase contrast imaging device using Talbot interference needs to be configured to capture the self-image of the phase grating 55. At this time, examples of parameters to be determined as setting of the device configuration include an interval of slits in the multi-slit 53b, a distance from the multi-slit 53b to the phase grating 55, an interval of phase shift sections in the phase grating 55, a distance from the phase grating 55 to the detector, and a pitch of detection elements in the detector. Unless these parameters are set optimally, the self-image of the phase grating 55 cannot be captured.

The radiation is radially emitted from the multi-slit 53b. Therefore, the self-image that appears on the detector is an image obtained by enlarging the phase grating 55 at a certain enlargement ratio. This enlargement ratio is determined by two parameters, a distance from the multi-slit 53b to the phase grating 55 and a distance from the phase grating 55 to the detector.

Depending on an imaging purpose, it is preferable in some cases to decrease the enlargement ratio to low magnification to capture the overall subject, and it is preferable in other cases to increase the enlargement ratio to high magnification to capture enlarged part of the subject. Since a position of the subject can be changed relatively freely for general X-ray imaging, it is not so difficult to capture an image of the subject at a favorite enlargement ratio. However, the radiation phase contrast imaging device is in circumstances that when the position of the subject is changed, the subject goes away from the phase grating 55, and thus it becomes difficult to capture clear images. When the subject is distant from the phase grating 55, it is difficult to capture an image of disturbance of the self-image.

From such circumstances, imaging using the radiation phase contrast imaging device of a conventional configuration has a narrow range of applicable enlargement ratio. Also, if the position of the subject is moved to the multi-slit 53b side, it is certain that part of the subject is greatly enlarged and reflected in the self-image, but disturbance of the self-image becomes slight, and it will become eventually impossible to fully take out internal information on the subject.

The present invention has been made in view of such circumstances, and an object of the present invention is to provide a radiation phase contrast imaging device that can deal with various imaging purposes.

Solution to Problem

In order to solve the above-described problem, the present invention has the following configuration.

That is, a radiation phase contrast imaging device according to one aspect of the present invention includes: (A1) a radiation source configured to emit a radiation; (B) a multi-slit in which a plurality of slits is arranged, the multi-slit being configured to make a phase of the radiation uniform by transmitting the radiation generated from the radiation source; a grating including linear structures arranged; a detector configured to detect a self-image of the grating or a shadow produced through absorption by the grating, the detector including detection elements arranged longitudinally and latitudinally, the detection elements detecting the radiation; (P1) a slit arrangement pitch change unit configured to change an arrangement pitch of the slits related to the multi-slit at a position through which the radiation emitted from the radiation source passes; and (Q1) a grating change unit configured to change an arrangement pitch of the structures related to the grating and a distance between the grating and the detector when the arrangement pitch of the slits is changed.

[Operations and effects] The present invention can provide a radiation phase contrast imaging device that can deal with various imaging purposes. That is, the device of the present invention can change the arrangement pitch of the slits related to the multi-slit and the arrangement pitch of the structures related to the grating. A positional relationship among the multi-slit, the grating, and the detector is determined based on the arrangement pitch of the slits related to the multi-slit, the arrangement pitch of the structures related to the grating, and the arrangement pitch of the detection elements related to the detector. Among these arrangement pitches, by changing the arrangement pitch of the slits and the arrangement pitch of the structures, the present invention can change the positional relationship among the multi-slit, the grating, and the detector. When the positional relationship among the multi-slit, the grating, and the detector is changed, the enlargement ratio of the self-image of the grating reflected in the detector can be changed. With such a configuration, the present invention can deal with various imaging purposes.

Note that when the arrangement pitch of the slits and the arrangement pitch of the structures are changed, it becomes unnecessary to change the arrangement pitch of the detection elements related to the detector when the enlargement ratio of the self-image is changed. Such a configuration makes it possible to change the enlargement ratio while using the same detector.

Also, in the radiation phase contrast imaging device, more preferably, the multi-slit includes a plurality of portions different in the arrangement pitch of the slits, and the slit arrangement pitch change unit implements change in the arrangement pitch of the slits by moving the multi-slit relative to the radiation source.

[Operations and effects] The above description represents a specific configuration of the present invention. Changing the arrangement pitch of the slits as described above makes it possible to change the pitch securely.

Also, more preferably, the radiation phase contrast imaging device further includes a plurality of the multi-slits different in the arrangement pitch of the slits, and the slit arrangement pitch change unit implements change in the arrangement pitch of the slits by switching which of the plurality of the multi-slits to transmit the radiation.

[Operations and effects] The above description represents a specific configuration of the present invention. Changing the arrangement pitch of the slits as described above makes it possible to change the pitch securely.

Also, in the radiation phase contrast imaging device, more preferably, the grating includes a plurality of portions different in the arrangement pitch of the structures, and the structure arrangement pitch change unit implements change in the arrangement pitch of the structures by moving the grating relative to the radiation source.

[Operations and effects] The above description represents a specific configuration of the present invention. Changing the arrangement pitch of the structures as described above makes it possible to change the pitch securely.

Also, more preferably, the radiation phase contrast imaging device further includes a plurality of the gratings different in the arrangement pitch of the structures, and the structure arrangement pitch change unit implements change in the arrangement pitch of the structures by switching which of the plurality of the gratings to transmit the radiation.

[Operations and effects] The above description represents a specific configuration of the present invention. Changing the arrangement pitch of the structures as described above makes it possible to change the pitch securely.

Also, more preferably, the radiation phase contrast imaging device performs imaging of a phase change by a fringe scanning method or moire one imaging method.

[Operations and effects] As described above, the present invention is also applicable to a device that performs imaging by the fringe scanning method or moire one imaging method Also, a radiation phase contrast imaging device according to one aspect of the present invention includes: (A2) a radiation source configured to make a phase of radiations uniform by arrangement of targets that emit the radiations; a grating including linear structures arranged; a detector configured to detect a self-image of the grating or a shadow produced through absorption by the grating, the detector including detection elements arranged longitudinally and latitudinally, the detection elements detecting the radiation; (P2) a target pitch change unit configured to change an arrangement pitch of the targets that emit the radiations in the radiation source; and (Q2) a grating change unit configured to change an arrangement pitch of the structures related to the grating and a distance between the grating and the detector when the arrangement pitch of the targets is changed.

[Operations and effects] The present invention is also applicable to a configuration that does not include a multi-slit. The above-described configuration includes a plurality of targets instead of the multi-slit. When the arrangement pitch of the targets is changed, an effect similar to an effect of changing the arrangement pitch of the slits in the multi-slit is obtained.

Advantageous Effects of Invention

The present invention can provide a radiation phase contrast imaging device that can deal with various imaging purposes. That is, the device of the present invention can change the arrangement pitch of the slits related to the multi-slit and the arrangement pitch of the structures related to the grating. A positional relationship among the multi-slit, the grating, and the detector is determined based on the arrangement pitch of the slits related to the multi-slit, the arrangement pitch of the structures related to the grating, and the arrangement pitch of the detection elements related to the detector. Among these arrangement pitches, by changing the arrangement pitch of the slits and the arrangement pitch of the structures, the present invention can change the positional relationship among the multi-slit, the grating, and the detector.

DESCRIPTION OF EMBODIMENT

An embodiment for executing the present invention will be described below with reference to the drawings. An X-ray corresponds to a radiation according to the present invention, and FPD is an abbreviation for flat panel detector.

First Embodiment

Figure 1:
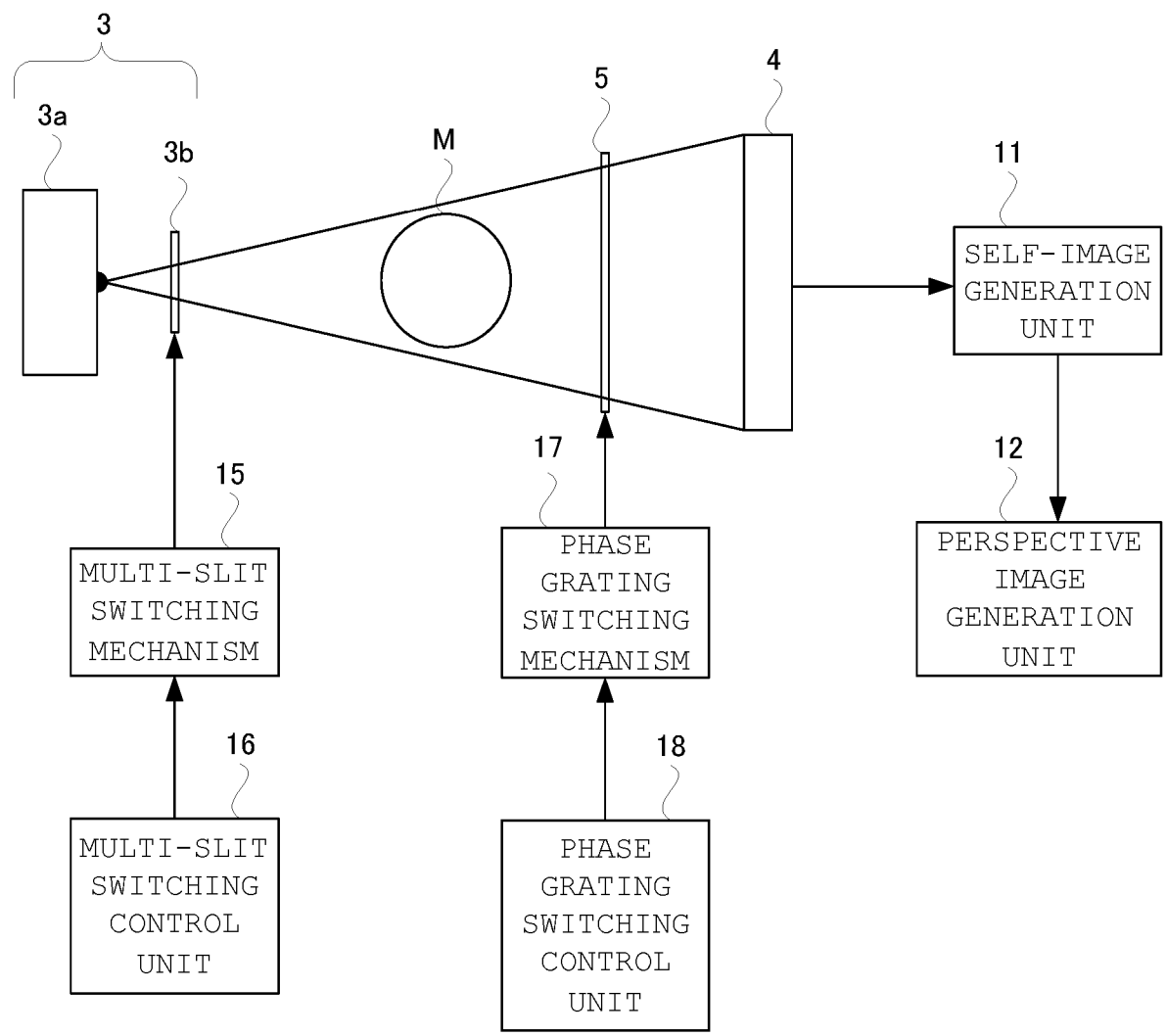
FIG. 1 is a functional block diagram describing an overall configuration of an X-ray phase contrast imaging device according to a first embodiment.

FIG. 1 is a diagram showing an overall configuration of an X-ray phase contrast imaging device 1 according to the present invention. As shown in FIG. 1, the configuration of the X-ray phase contrast imaging device according to the present invention includes an X-ray source 3a that emits an X-ray toward a subject M, and an FPD 4 that detects the X-ray that is transmitted through the subject M. The X-ray source 3a emits the X-ray from the left side toward the right side of paper of FIG. 1. The X-ray emitted at this time is a beam having a certain degree of expansion. The FPD 4 includes a detection surface that detects the X-ray. The FPD 4 detects a self-image of a phase grating 5 or a shadow produced by absorption by the grating to be described later. The FPD 4 corresponds to a detector of the present invention. The X-ray source 3a corresponds to a radiation source of the present invention, and the FPD 4 corresponds to the detector of the present invention. The phase grating 5 corresponds to the grating of the present invention.

Figure 2:
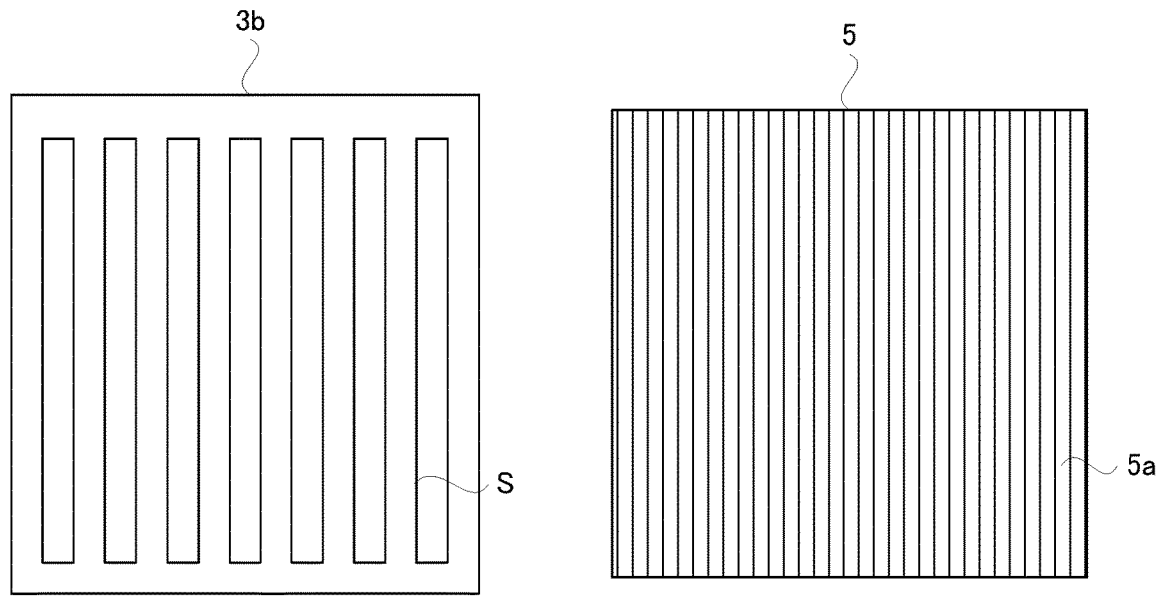
FIG. 2 is a plan view describing a configuration of a multi-slit and a phase grating according to the first embodiment.

Various components regarding Talbot interference are attached between the X-ray source 3a and the FPD 4. A multi-slit 3b that makes a phase of the X-ray uniform is provided near the X-ray source 3a. This multi-slit 3b is formed of a material that does not transmit the X-ray as shown on the left side of FIG. 2, and longitudinally elongated through holes (slits S) are arranged laterally. Therefore, part of the X-ray entering the multi-slit 3b can pass the multi-slit 3b through the slits S. This multi-slit 3b is provided for the purpose of clarifying the self-image of the phase grating 5 to be described later. The X-ray generated by the X-ray source 3a is ideally generated at one specified point, expands radially from the point, and heads for the FPD 4. However, the actual X-ray source 3a has a wide area with positions different from each other, and the X-ray is generated from the area. Then, the X-rays generated at different generation positions overlap each other, and head for the phase grating 5 to be described later. Since the X-rays passing through the phase grating 5 are not generated at one point, an image of the phase grating 5 (self-image to be described later) will blur.

In order to prevent such a blur, it is required at least to provide a slit between the X-ray source 3a and the phase grating 5 to bring the X-rays close to an ideal state of being emitted from one specified point. However, only with a single slit, a dose of the X-rays is insufficient, and a clear image of the phase grating 5 cannot be obtained. Therefore, the configuration of the first embodiment includes the multi-slit 3b having a plurality of slits. By preparing the plurality of slits that transmits the X-rays, the number of slits as a light source that emits the X-rays increases. Therefore, according to the first embodiment, the dose of the X-rays is larger as compared to a case where a single slit is provided, and the dose of the X-rays is sufficient.

The X-rays generated from the multi-slit 3b, which are transmitted through the plurality of slits S different from each other in position, are not an X-ray beam emitted from one specified point. However, if a careful consideration is given to an interval between the slits S in the multi-slit 3b to make a specified interval, images of the phase grating 5 related to the X-ray beams emitted from respective slits S appear in the same phase on the FPD 4, and the images overlap each other and strengthen each other. In this way, the images of the phase grating 5 are captured with a sufficient X-ray dose without a blur.

Aside from the multi-slit 3b, the phase grating 5 is provided between the X-ray source 3a and the FPD 4. This phase grating 5 has a configuration in which linear phase shift sections extending longitudinally are arranged laterally, as shown on the right side of FIG. 2. These phase shift sections have characteristics to change the phase of the X-ray. Therefore, when the phase grating 5 transmits the X-rays, the phase of the X-ray entering the phase shift section changes there, whereas the X-ray entering between the two phase shift sections is transmitted as it is. The self-image indicating a pattern of the phase grating 5 is projected on the FPD 4. It is to be noted that this self-image is not a mere projection image of the phase grating 5. The self-image is an interference fringe generated on the FPD 4 by the X-ray interfered by the phase grating 5. The self-image is detected by the FPD 4. A direction in which the phase shift sections extend corresponds to a vertical direction of paper of FIG. 1. The phase grating 5 has a configuration in which the X-ray-absorbing phase shift sections extending longitudinally are arranged laterally, and Talbot interference is generated when the X-rays are transmitted. A direction in which the slits S in the multi-slit 3b extend agrees with the direction in which the phase shift sections in the phase grating 5 extend. The phase shift sections correspond to structures of the present invention. A longitudinal direction for detection elements 4p arranged longitudinally and latitudinally on the FPD 4 agrees with the direction in which the phase shift sections extend.

The phase grating 5 has a configuration in which the linear phase shift sections 5a that interact with the X-ray are arranged. The interaction of the X-ray refers to an effect of changing the phase of the X-ray. In particular, when the phase grating 5 has a configuration of investigating the effect of absorbing the X-ray, the phase grating 5 may not be called phase grating, but may be called absorption grating. It is to be noted that this absorption grating is a concept different from an absorption grating 6 to be described in FIG. 17.

Figure 3:
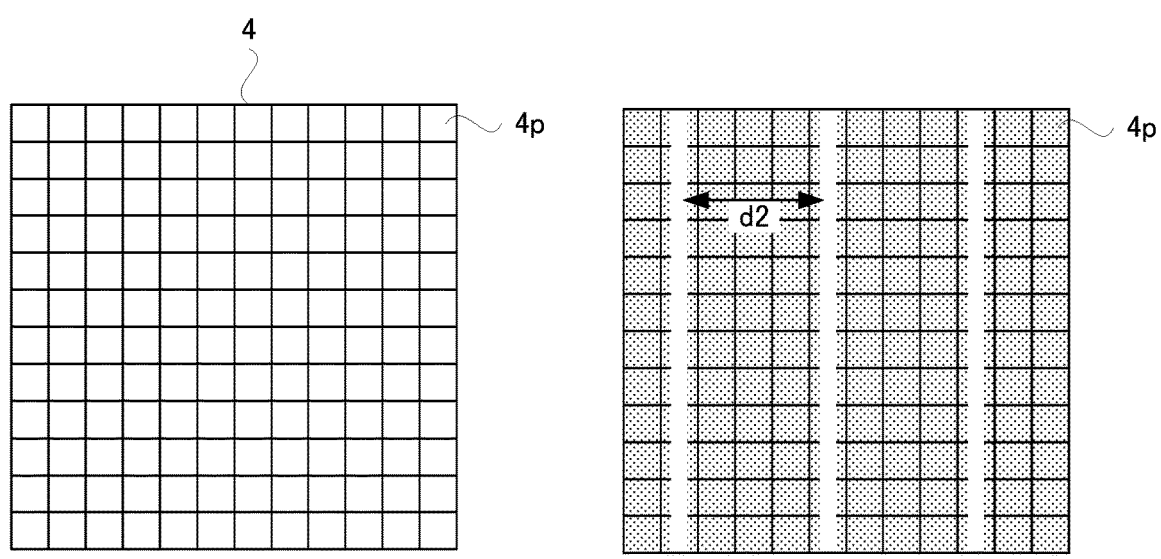
FIG. 3 is a plan view describing a configuration of an FPD according to the first embodiment.

The left side of FIG. 3 shows the detection surface that detects the X-ray in the FPD 4. The detection elements 4p are arranged longitudinally and latitudinally on the detection surface of the FPD 4. The right side of FIG. 3 shows the self-image of the phase grating 5 being reflected on the detection surface of the FPD 4. That is, areas sandwiched between the phase shift sections of the phase grating 5 adjacent to each other appear as bright belt-shaped lines on the detection surface. A direction in which the belt-shaped lines extend agrees with the longitudinal direction in an array of the detection elements 4p. The bright belt-shaped lines are arranged laterally, and an arrangement pitch of the bright belt-shaped lines is defined as d2. This arrangement pitch d2 is an integral multiple of the arrangement pitch of the detection elements 4p. When the pitches are made uniform in this way, the self-image is projected on the detection surface, enabling secure detection of the belt-shaped lines. The FPD 4 has a configuration in which the detection elements 4p are arranged longitudinally and latitudinally, the detection elements 4p detecting the self-image of the phase grating 5 produced by Talbot interference and detecting the X-ray. Note that although the belt-shaped lines are drawn as bright lines in FIG. 3, actual variation in density in the self-image is continuous. Therefore, a bright section and a dark section cannot be distinguished clearly as in FIG. 3. The belt-shaped lines are drawn as shown in FIG. 3 for reasons for convenience of subsequent descriptions.

Figure 4:
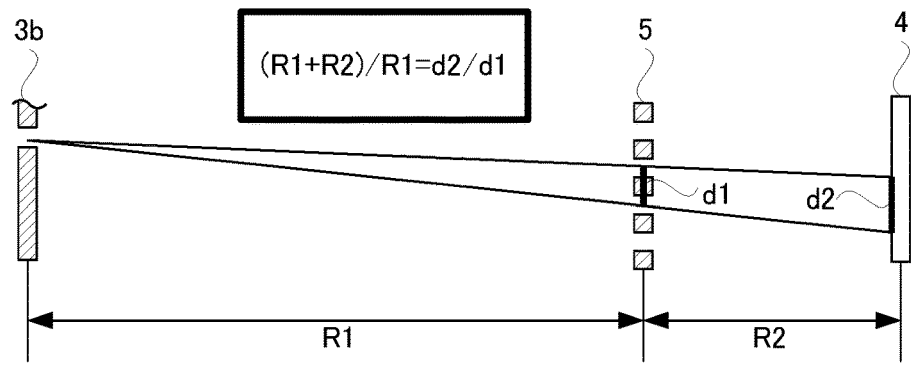
FIG. 4 is a schematic diagram describing a relationship between respective parameters according to the first embodiment.

FIG. 4 shows a positional relationship among the multi-slit 3b, the phase grating 5, and the FPD 4. It is assumed that a distance from the multi-slit 3b to the phase grating 5 is R1 and that a distance from the phase grating 5 to the detection surface of the FPD 4 is R2. Note that since the multi-slit 3b and the phase grating 5 have predetermined thicknesses, a reference position is needed in order to determine each position. Therefore, it is assumed that a position of a center in a thickness direction of the multi-slit 3b is the reference position. Similarly, it is assumed that a position of a center in a thickness direction of the phase grating 5 is the reference position.

As shown in FIG. 4, it is assumed that the X-ray is emitted from one of the slits S the multi-slit 3b has. This X-ray heads for the phase grating 5 while expanding gradually. Here, attention is paid to one of the phase shift sections the phase grating 5 has. Consider a path of the X-ray that passes through an upper side of the phase shift section and heads for the FPD 4, and a path of the X-ray that passes through a lower side of the phase shift section and heads for the FPD 4. The X-ray passing along the upper path is projected on a bright line that appears on the detection surface of the FPD 4. The X-ray passing along the lower path is also projected on the bright line that appears on the detection surface, but the bright line projected differs from the bright line related to the upper path. The X-ray passing along the upper path is projected on the bright line that appears on the upper side on the detection surface, whereas the X-ray passing along the lower path is projected on the bright line that appears on the lower side on the detection surface. These bright lines, which are adjacent to each other, are apart from each other by the arrangement pitch d2 of the bright lines.

Here, consider a distance between a position of a point through which the upper path in the phase grating 5 passes, and a position of a point through which the lower path passes. This distance agrees with an arrangement pitch d1 of the phase shift sections 5a.

It is assumed that the X-ray is emitted from one of the slits S the multi-slit 3b has. At this time, consider to what extent the phase grating 5 is enlarged and projected on the FPD 4. The enlargement ratio of the phase grating 5 is equal to (R1+R2)/R1, considering the positional relationship among the multi-slit 3b, the phase grating 5, and the FPD 4. Meanwhile, in the phase grating 5, a length of the arrangement pitch d1 of the phase shift sections 5a is enlarged to a length of the arrangement pitch d2 of the bright lines of the self-image by the X-ray beam expanding radially from a starting point of the slits S of the multi-slit 3b, and is reflected on the detection surface. From the aforementioned circumstances, the enlargement ratio of the phase grating 5 is d2/d1. The enlargement ratios calculated from these two viewpoints should be the same value. Therefore, the following equation holds.

$$(R1+R2)/R1 = d2/d1 \tag{1}$$

This equation assumes a $\pi/2$ phase grating. For a $\pi$ phase grating, the right-hand side is $\tfrac{1}{2} \cdot d2/d1$. Although the present invention is applicable to the $\pi$ phase grating as well, subsequent descriptions assume that the phase grating 5 is the $\pi/2$ phase grating.

Figure 5:
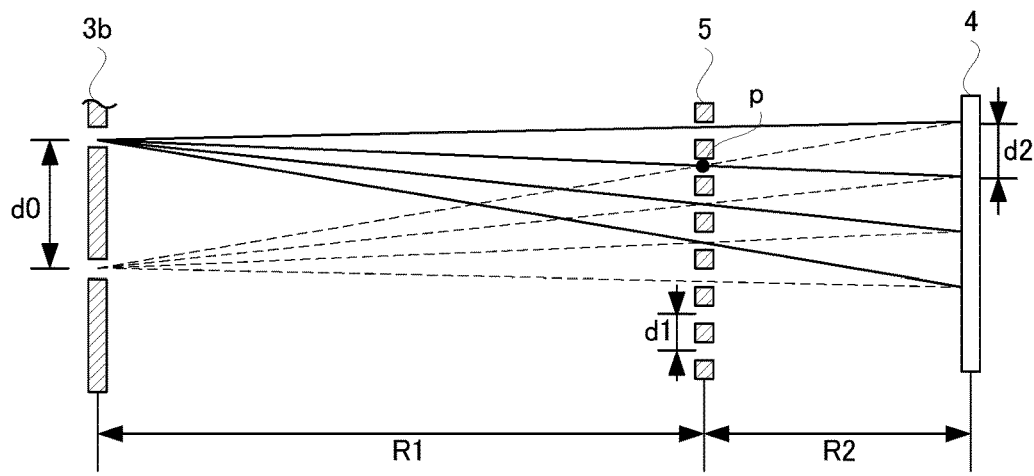
FIG. 5 is a schematic diagram describing the relationship between respective parameters according to the first embodiment.

Next, it is assumed that the arrangement pitch of the slits S in the multi-slit 3b is d0. Since a similar equation can be derived for this arrangement pitch d0, this point will be described. Here, it is assumed that the X-rays are radially emitted from two slits S adjacent to each other on the multi-slit 3b. A distant apart between these two slits S is the arrangement pitch d0. FIG. 5 shows the X-rays emitted from the upper slit S in solid lines, and the X-rays emitted from the lower slit S in dotted lines.

The X-rays emitted from the upper slit S become a pattern in which the bright lines are arranged at equal intervals by passing through the phase grating 5, and reach the detection surface of the FPD 4. Similarly, the X-rays emitted from the lower slit S also become a pattern in which the bright lines are arranged at equal intervals by passing through the phase grating 5, and reach the detection surface of the FPD 4. In order for the self-image of the phase grating 5 to appear on the detection surface, the pattern related to the upper slit S and the pattern related to the lower slit S need to overlap so as to strength each other.

Attention is paid to a position p sandwiched between the two phase shift sections 5a that constitute the phase grating 5. This position p is a transit point through which the X-rays emitted from the plurality of slits S that constitute the multi-slit 3b pass on the way to the FPD 4. FIG. 5 shows the X-rays that are emitted from the upper slit S on the multi-slit 3b passing through the position p and heading for the FPD 4, and the X-rays that are emitted from the lower slit S passing through the position p and heading for the FPD 4.

Figure 6:
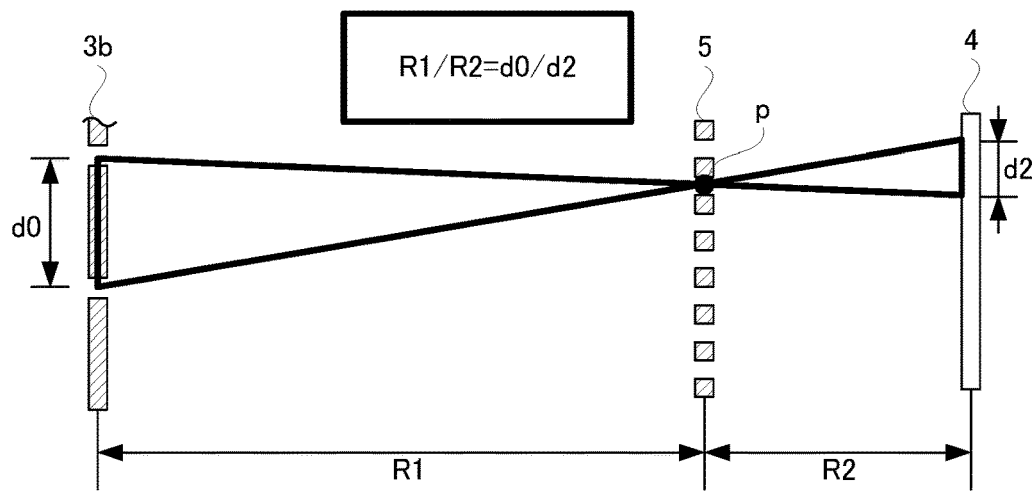
FIG. 6 is a schematic diagram describing the relationship between respective parameters according to the first embodiment.

FIG. 6 extracts and draws the X-rays shown in FIG. 5 that pass through the position p. The path related to the upper slit S and the path related to the lower slit S cross at the position p. Considering the position p as a center, two triangles appear on the right side and the left side. The triangle that appears on the left side of the position p is a straight line connecting the slits S, a straight line connecting the upper slit S and the position p, and a straight line connecting the lower slit S and the position p. Meanwhile, the triangle that appears on the right side of the position p is a straight line connecting the bright lines that appear on the FPD 4, a straight line connecting the position p and the upper bright line, and a straight line connecting the lower bright line and the position p. These two triangles have similar figures. A ratio of sizes of the two triangles is R1:R2. A length of the straight line connecting the slits S is d0, and a length connecting the bright lines on the FPD 4 is d2. Therefore, the following equation holds.

$$R1/R2 = d0/d2 \quad (2)$$

Therefore, the positional relationship among the multi-slit 3b, the phase grating 5, and the FPD 4, the arrangement pitch d0 of the slits S the multi-slit 3b has, and the arrangement pitch d1 of the phase shift sections 5a in the phase grating 5 need to have a configuration that satisfies the above-described two equations. Also, an arrangement pitch d3 of the detection elements 4p of the FPD 4 is determined based on the arrangement pitch d2 of the bright lines of the self-image of the phase grating 5. Therefore, this arrangement pitch d3 also needs to be determined according to the two equations above. The arrangement pitches d2 and d3 have the following relationship, where n is an integer (refer to FIG. 3 and the description regarding FIG. 3 for details).

$$d2 = n \cdot d3$$

Therefore, the two equations calculated from FIG. 4 and FIG. 6 can be represented through rewriting as follows.

$$(R1+R2)/R1 = n \cdot d3/d1$$

$$R1/R2 = d0/n \cdot d3$$

These two equations show that setting of the arrangement pitch d3 of the detection elements 4p is also determined based on the positional relationship among the multi-slit 3b, the phase grating 5, and the FPD 4, the arrangement pitch d0 of the slits S the multi-slit 3b has, and the arrangement pitch d1 of the phase shift sections 5a in the phase grating 5.

<About Enlargement of Subject Image>

Figure 7:
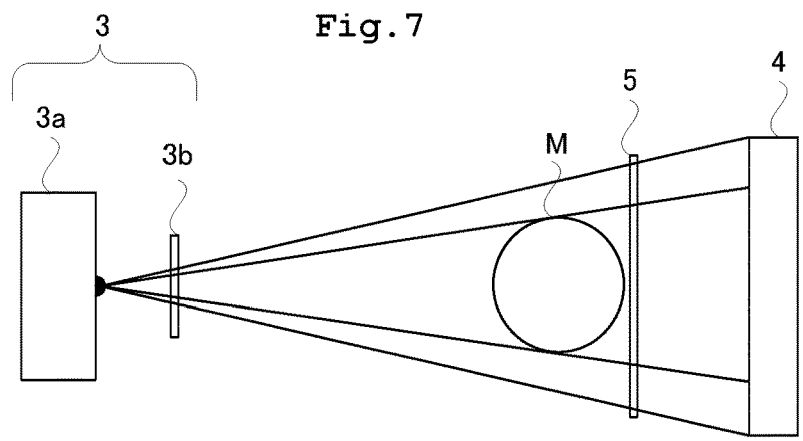
FIG. 7 is a schematic diagram describing a position of a subject according to the first embodiment.

Next, depending on placement of the subject M, the self-image appears differently on the FPD 4. This point will be described. FIG. 7 shows a case where the subject M is placed near the FPD 4. The X-rays passed through the multi-slit 3b expand radially, pass through the subject M and the phase grating 5, and reach the FPD 4. At this time, when a distance between the subject M and the FPD 4 is short, the subject image will reach the FPD 4 without being enlarged greatly. Since the subject image appears as disturbance of the self-image in X-ray phase contrast imaging, when the distance between the subject M and the FPD 4 is short, the self-image with only a peripheral part disturbed will be obtained. In order to observe the overall subject M securely, the subject M is preferably placed close to the FPD 4, as shown in FIG. 7.

Figure 8:
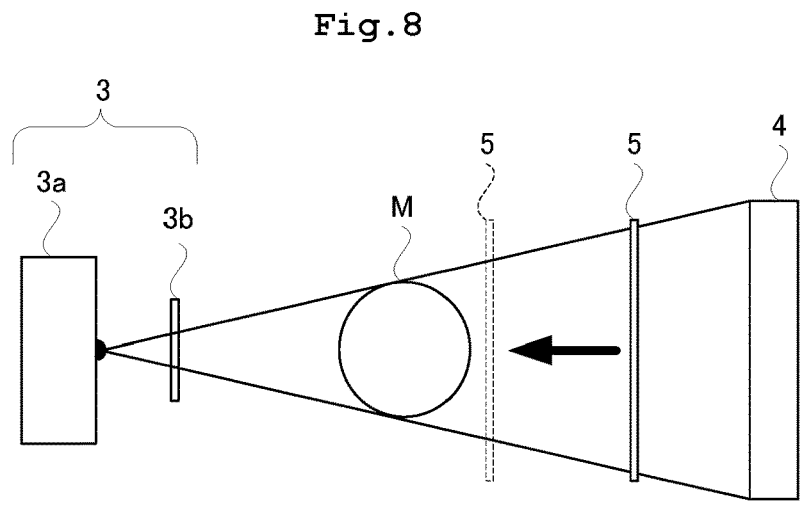
FIG. 8 is a schematic diagram describing the position of the subject according to the first embodiment.

FIG. 8 shows a case where the subject M is brought close to the X-ray source 3a with the positional relationship among the X-ray source 3a, the multi-slit 3b, the phase grating 5, and the FPD 4 identical to the configuration of FIG. 7. The X-rays passed through the multi-slit 3b expand radially, pass through the subject M and the phase grating 5, and reach the FPD 4. At this time, when the distance between the subject M and the FPD 4 is long, the subject image will be enlarged greatly and reach the FPD 4. Since the subject image appears as disturbance of the self-image in X-ray phase contrast imaging, when the distance between the subject M and the FPD 4 is long, the entirely disturbed self-image will be obtained. In order to observe the subject M with its part enlarged, the subject M is preferably placed away from the FPD 4, as shown in FIG. 8.

In fact, the positional relationship among the multi-slit 3b, the phase grating 5, and the FPD 4 shown in FIG. 7 is suitable for capturing the subject M at the enlargement ratio of low magnification, and is not suitable for capturing the subject M at the enlargement ratio of high magnification. In FIG. 8, although the subject M is captured at the enlargement ratio of high magnification, the positional relationship among the multi-slit 3b, the phase grating 5, and the FPD 4 is the same as that in FIG. 7. Therefore, in FIG. 8, the multi-slit 3b, the phase grating 5, and the FPD 4 are placed inappropriately. In order to make an appropriate arrangement of the multi-slit 3b, the phase grating 5, and the FPD 4, it is necessary to bring the phase grating 5 closer to the subject M, as shown in a dotted line.

Figure 9:
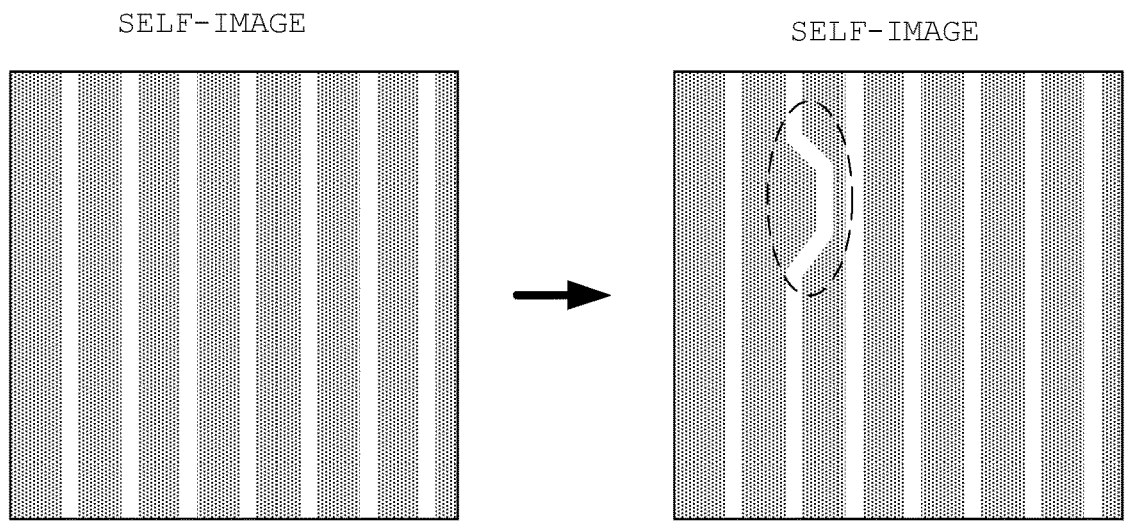
FIG. 9 is a schematic diagram describing a self-image according to the first embodiment.

The necessity to bring the phase grating 5 close to the subject M will be described. The left side of FIG. 9 shows the self-image of the phase grating 5 obtained with the subject M not mounted. The self-image has a configuration in which stripe-shaped bright lines are arranged. Meanwhile, the right side of FIG. 9 shows the self-image of the phase grating 5 obtained with the subject M mounted. The self-image is partially shifted laterally under the influence of the subject M. A state of this shift is shown surrounded by a dotted line on the right side of FIG. 9. This disturbance of the self-image shows an internal structure of the subject M. This means that, in order to know the internal structure of the subject M, preferably, the self-image is greatly disturbed. When the disturbance of the self-image is small, information about the subject M will decrease.

Figure 10:
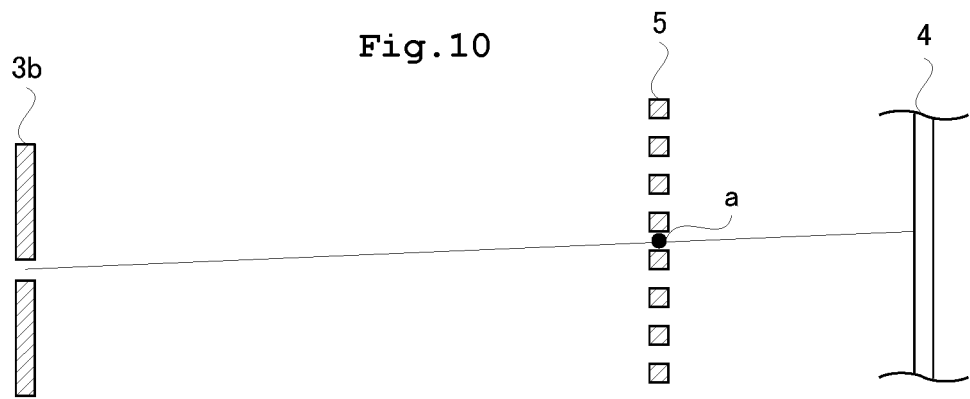
FIG. 10 is a schematic diagram describing a positional relationship between the subject and the phase grating according to the first embodiment.

In order to greatly disturb the self-image, it is necessary to place the subject M and the phase grating close to each other. This circumstance will be described. FIG. 10 describes a bright line that appears on the FPD 4. This bright line appears on the FPD 4 by the X-ray emitted from the multi-slit 3b and expanding radially passing through the phase grating 5 and reaching the FPD 4. The multi-slit 3b has the plurality of slits S, and when one of which is paid attention to, the X-ray passed through the slit S reaches the FPD 4 along the path shown in FIG. 10. The bright line appears at a position at which the path of the X-ray and the FPD 4 cross. It is assumed that this path passes through a position "a" of the phase grating 5.

How this bright line is shifted by the subject M will be considered.

Figure 11:
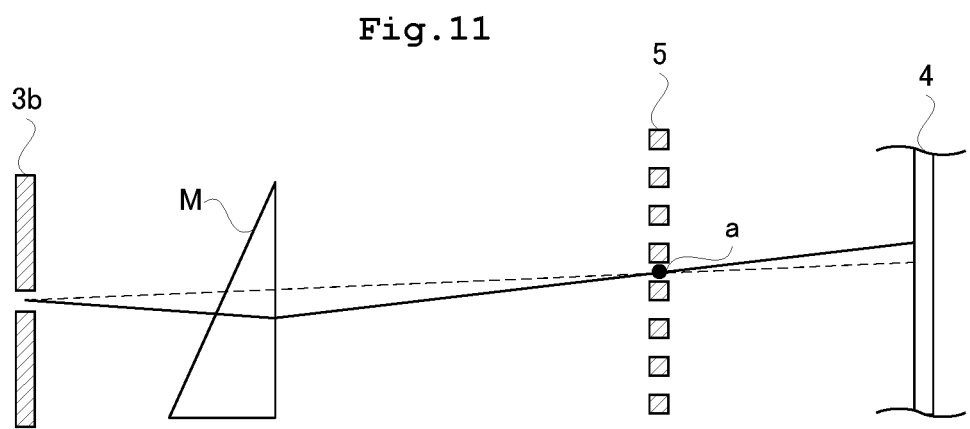
FIG. 11 is a schematic diagram describing the positional relationship between the subject and the phase grating according to the first embodiment.

FIG. 11 shows a case where the subject M is placed between the multi-slit 3b and the phase grating 5 in FIG. 10. In FIG. 11, the X-ray, which is affected by the subject M, will not travel along the path that is described in FIG. 10 and shown in a dotted line of FIG. 11. Nevertheless, part of the X-ray emitted from the slit S shown in FIG. 10 out of the slits S of the multi-slit 3b passes through the position "a" of the phase grating 5, and then reaches the FPD 4. Such an X-ray passes through the phase grating 5 along the path shown in a solid line of FIG. 11.

The path in a broken line is the same as the path in the solid line in that the paths pass through the position "a" of the phase grating 5. However, since there is a phase difference between the X-ray passing along the path in the broken line and the X-ray passing along the path in the solid line, bright line positions on the FPD 4 do not agree with each other. This difference in the bright line positions corresponds to the disturbance of the self-image under the influence of the subject M.

Figure 12:
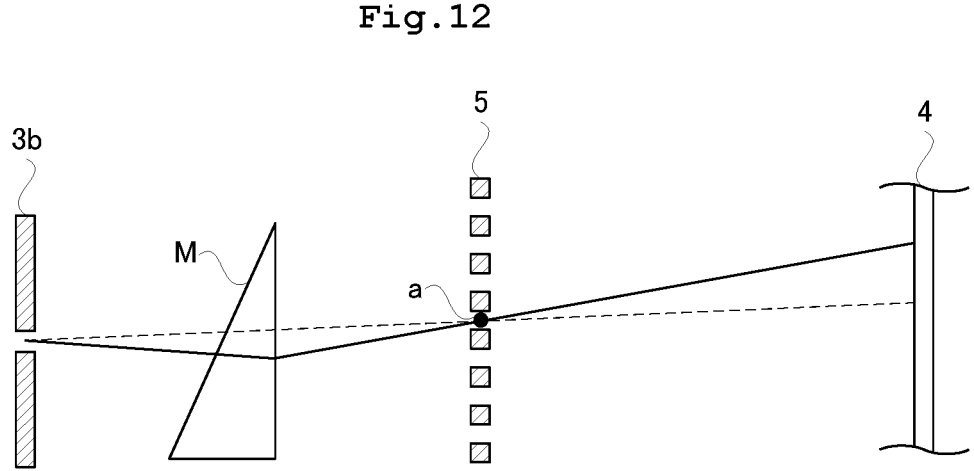
FIG. 12 is a schematic diagram describing the positional relationship between the subject and the phase grating according to the first embodiment.

FIG. 12 shows a state where the phase grating 5 is brought close to the subject M in FIG. 11. When the subject M does not exist while the multi-slit 3b, the phase grating 5, and the FPD 4 remain in this positional relationship, the X-ray passing through the position "a" of the phase grating 5 travels along the path shown in the broken line and reaches the FPD 4. The position reached by the broken line on the FPD 4 shows the position where the bright line appears without the subject M. Next, when the subject M exists, the X-ray passing through the position "a" of the phase grating 5 travels along the path shown in a solid line and reaches the FPD 4. The position reached by the solid line on the FPD 4 shows the position where the bright line appears with the subject M. The path in a broken line is the same as the path in the solid line in that the paths pass through the position "a" of the phase grating 5. However, since incident directions differ, arrival positions on the FPD 4 differ. This difference in the arrival positions corresponds to the disturbance of the self-image under the influence of the subject M.

A comparison between FIG. 11 and FIG. 12 will lead to realization that the bright line of the self-image shifts more greatly in FIG. 12 as compared to a case in FIG. 11. Even if the direction of the X-ray passing through the position "a" differs only slightly depending on the existence of the subject M, the difference appears larger on the FPD 4 in FIG. 12. As a distance between the FPD 4 and the phase grating 5 increases, the difference in the traveling direction of the X-ray increases, resulting in the shift of the bright line in the self-image of the phase grating 5.

From such circumstances, when the subject M is moved in order to change the enlargement ratio of the subject M in the self-image, essentially, the phase grating 5 is also preferably moved following the subject M. However, the arrangement pitch d1 of the phase shift sections 5a in the phase grating 5, the arrangement pitch d0 of the slits S in the multi-slit 3b, and the arrangement pitch d3 of the detection elements 4p in the FPD 4 are fixed. When the phase grating 5 is displaced, each parameter does not satisfy the above-described two equations. As a result, the self-image of the phase grating 5 stops appearing on the detection surface of the FPD 4, or the FPD 4 cannot detect the self-image because the arrangement pitch of the bright lines in the self-image changes.

<Most Characteristic Configuration of the Present Invention>

From the aforementioned circumstances, the present invention changes the configuration of the multi-slit 3b and the phase grating 5 between a mode for low magnification imaging and a mode for high magnification imaging.

Figure 13:
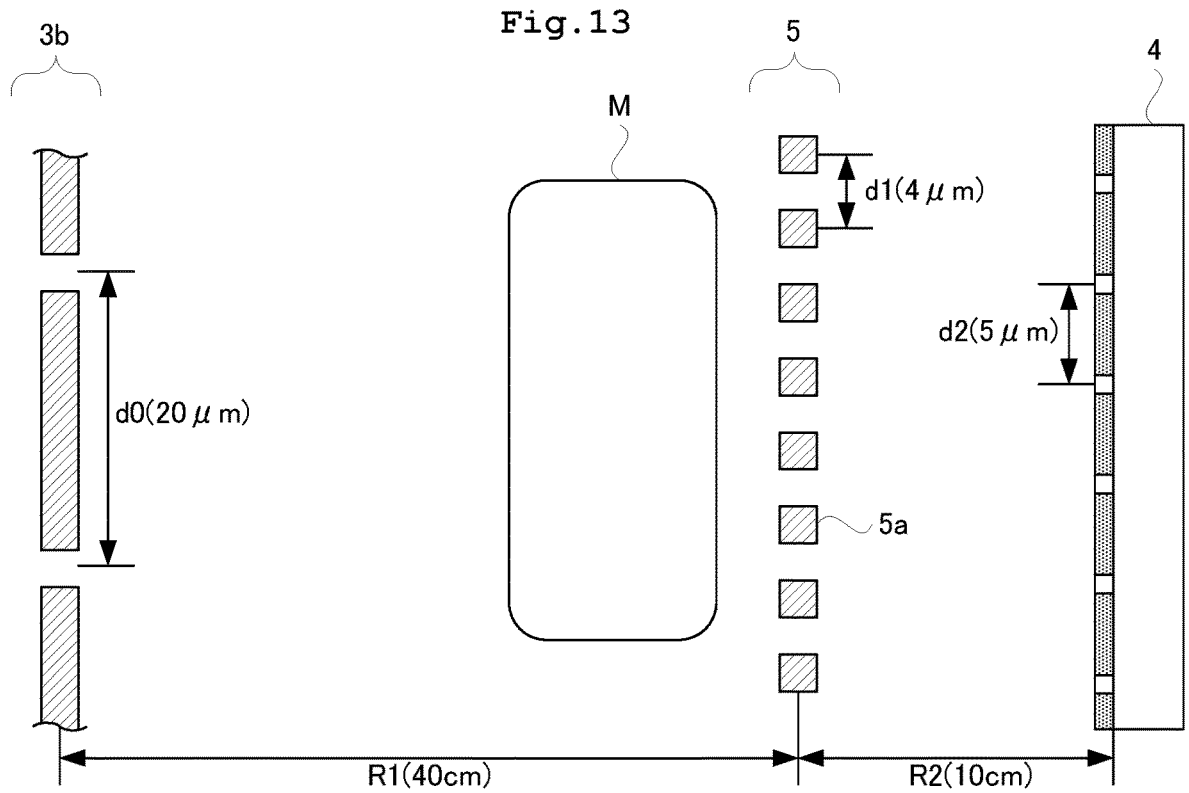
FIG. 13 is a schematic diagram describing various parameters in a low magnification mode according to the first embodiment.

FIG. 13 shows the configuration of the multi-slit 3b, the phase grating 5, and the FPD 4 in the mode for low magnification imaging. With this configuration, a distance R1 between the multi-slit 3b and the phase grating 5 is 40 cm, and a distance between the phase grating 5 and the detection surface of the FPD 4 is 10 cm. This configuration corresponds to FIG. 7 described above. In FIG. 13, the arrangement pitch d0 of the slits S in the multi-slit 3b is 20 the arrangement pitch of the phase shift sections in the phase grating 5 is 4 and the arrangement pitch d2 of the bright lines that constitute the self-image that appears on the FPD 4 is 5 μm.

Figure 14:
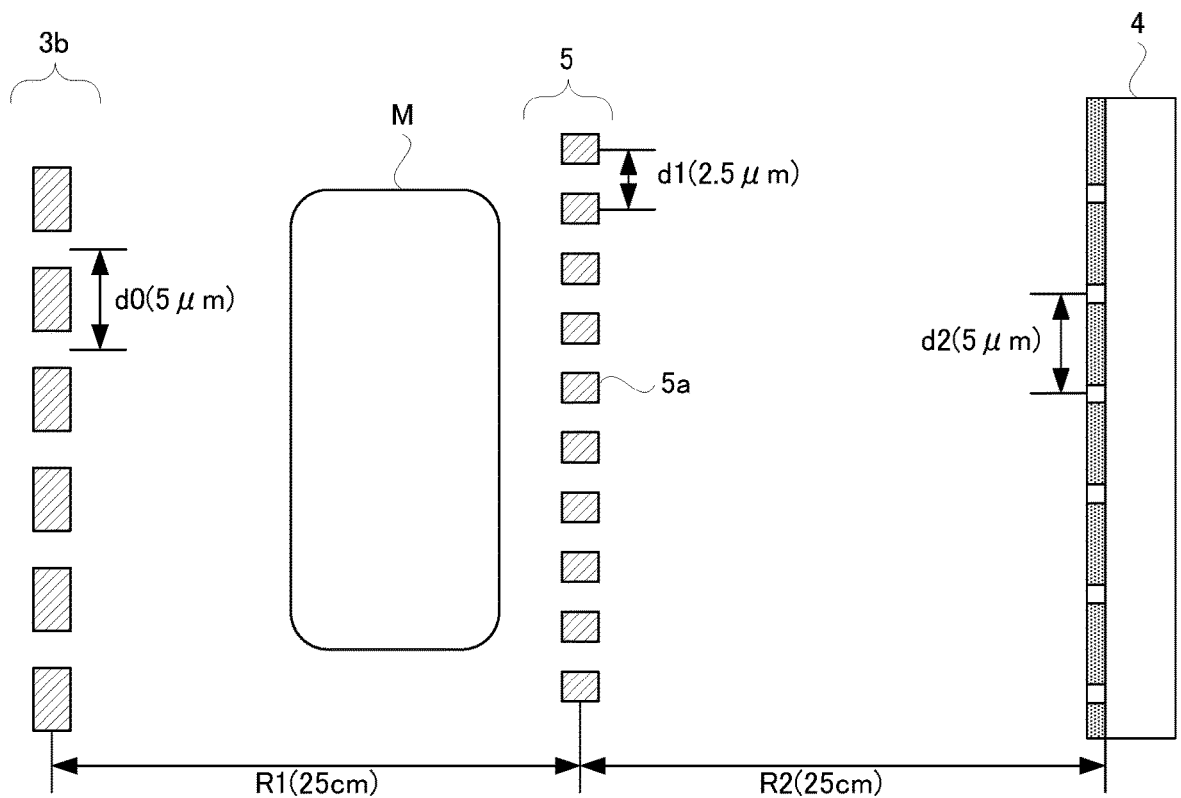
FIG. 14 is a schematic diagram describing various parameters in a high magnification mode according to the first embodiment.

FIG. 14 shows the configuration of the multi-slit 3b, the phase grating 5, and the FPD 4 in the mode for high magnification imaging. With this configuration, the distance R1 between the multi-slit 3b and the phase grating 5 is 25 cm, and the distance between the phase grating 5 and the detection surface of the FPD 4 is 25 cm. This configuration corresponds to FIG. 8 described above. In FIG. 14, the arrangement pitch d0 of the slits S in the multi-slit 3b is 5 μm, the arrangement pitch of the phase shift sections in the phase grating 5 is 2.5 μm, and the arrangement pitch d2 of the bright lines that constitute the self-image that appears on the FPD 4 is 5 μm.

In both modes, the arrangement pitch d2 is common, 5 μm. This is based on consideration that the same FPD 4 is used in both modes. The arrangement pitch of the detection elements 4p on the detection surface of the FPD 4 is determined by the arrangement pitch of the bright lines of the self-image. Therefore, when the arrangement pitch of the bright lines is common between the two modes, the same FPD 4 can be used in both modes.

Figure 15:
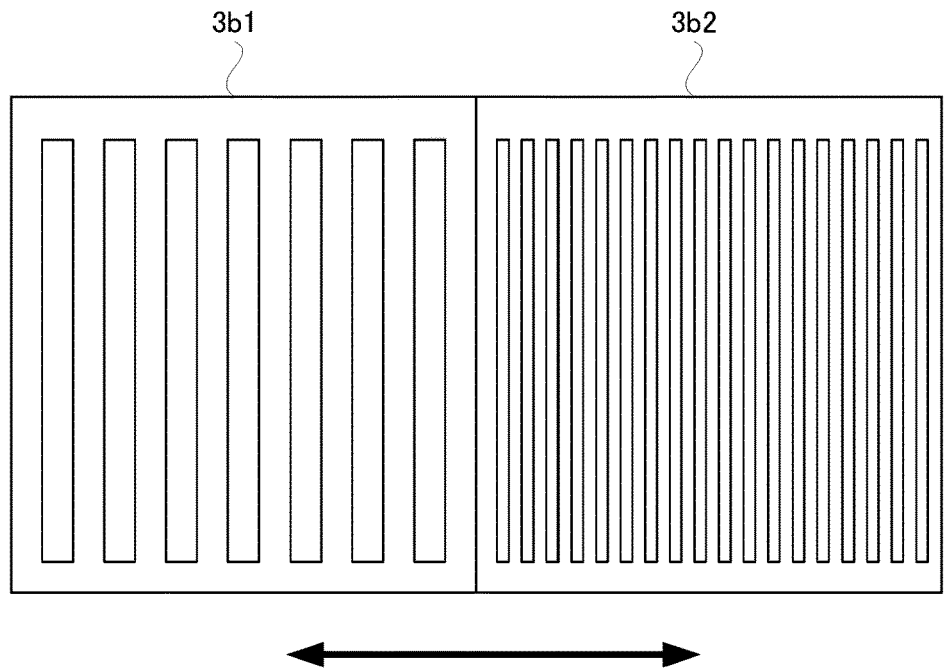
FIG. 15 is a schematic diagram describing switching of the multi-slit according to the first embodiment.

Therefore, the X-ray phase contrast imaging device according to the present invention includes two types of multi-slits 3b and two types of phase gratings 5. Among these configurations, FIG. 15 shows a configuration in which two types of multi-slits 3b1 and 3b2 different in the arrangement pitch d0 are arranged on one plane in the arrangement direction of the slits S and integrated. At this time, the slits S extend in the same direction between the two multi-slits 3b1 and 3b2. A multi-slit switching mechanism 15 described in FIG. 1 is configured to switch the multi-slits 3b1 and 3b2 positioned on the optical path of the X-ray by sliding the multi-slits 3b1 and 3b2 in the arrangement direction of the slits S. That is, when switching the imaging mode, the multi-slit switching mechanism 15 operates to switch the multi-slits 3b1 and 3b2. A multi-slit switching control unit 16 is provided for the purpose of controlling the multi-slit switching mechanism 15. The multi-slit switching mechanism 15 corresponds to a slit arrangement pitch change unit of the present invention.

With the configuration of the first embodiment, the multi-slit switching mechanism 15 changes the arrangement pitch of the slits S related to the multi-slit 3b at a position where the X-ray emitted from the X-ray source 3a toward the FPD 4 passes. The multi-slit 3b according to the present invention includes a plurality of portions different in the arrangement pitch of the slits S. The arrangement pitch of the slits S is changed by the multi-slit switching mechanism 15 moving the multi-slit 3b toward the X-ray source 3a.

Note that in FIG. 15, two multi-slits 3b1 and 3b2 are arranged in the arrangement direction of the slits S. However, the two multi-slits 3b1 and 3b2 may be arranged in the direction in which the slits S extend, and the multi-slits 3b1 and 3b2 may be switched by sliding the multi-slits 3b1 and 3b2 in the direction in which the slits S extend. Again, the direction in which the slits S extend is the same between the two multi-slits 3b1 and 3b2.

<Switching of Phase Grating>

Figure 16:
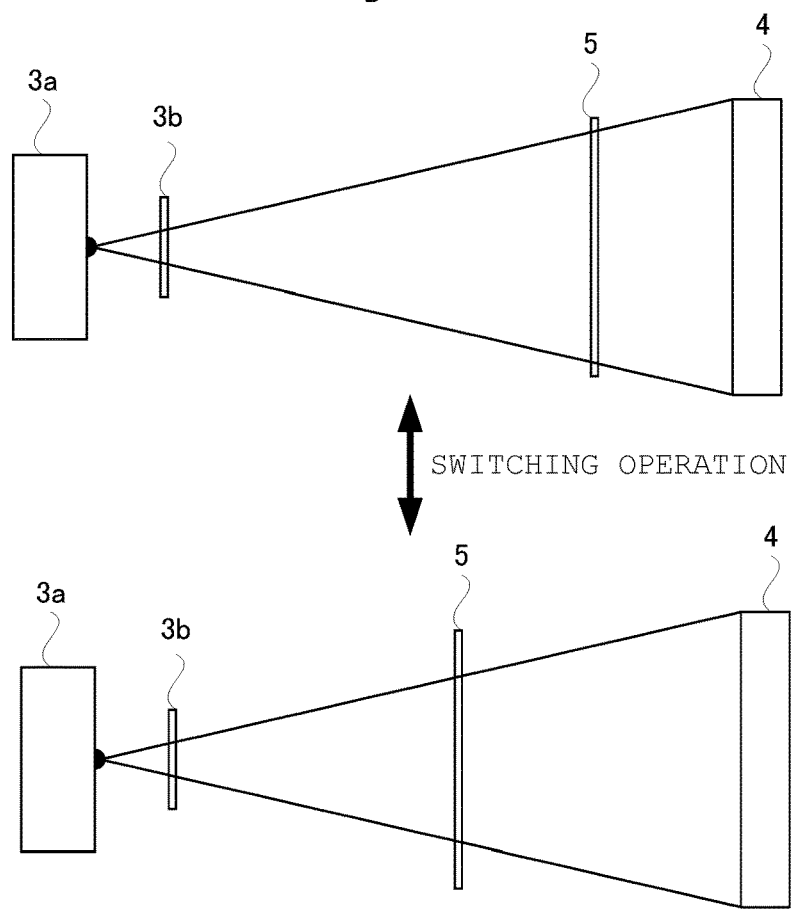
FIG. 16 is a schematic diagram describing switching of the phase grating according to the first embodiment.

FIG. 16 shows how two types of phase gratings 5a and 5b different in the arrangement pitch d1 are switched. A phase grating switching mechanism 17 described in FIG. 1 is configured to switch the phase grating 5 positioned on the optical path of the X-ray (placed at a position through which the X-ray emitted from the X-ray source 3a toward the FPD 4 passes). Positions where the two phase gratings 5a and 5b appear on the optical path of the X-ray differ from each other. That is, the phase grating 5a on a near side and the phase grating 5b on a far side as seen from the X-ray source 3a are provided. In accordance with the imaging mode, the phase grating 5a on the near side or the phase grating 5b on the far side is placed on the optical path of the X-ray. Therefore, when switching is performed between the two phase gratings 5a and 5b, the distance from the phase grating 5 to the FPD 4 changes. In accordance with this change, the distance from the multi-slit 3b to the phase grating 5 also changes. This distance change is implemented by a change in an insertion position of the phase grating 5 on the optical path from the multi-slit 3b to the FPD 4. Note that a phase grating switching control unit 18 is provided for the purpose of controlling the phase grating switching mechanism 17. The phase grating switching mechanism 17 corresponds to a grating change unit of the present invention.

With the configuration of the first embodiment, the phase grating switching mechanism 17 changes the arrangement pitch of the phase shift sections 5a related to the phase grating 5 at the position through which the X-ray emitted from the multi-slit 3b toward the FPD 4 passes. When the arrangement pitch of the slits S is changed, the phase grating switching mechanism 17 of the present invention changes the arrangement pitch of the phase shift sections related to the phase grating 5 and the distance R2 between the phase grating 5 and the FPD 4. This change is implemented by the phase grating switching mechanism 17 moving the two phase gratings 5 toward the X-ray source 3a to move the phase grating 5 on the optical path to outside the optical path, and to move the phase grating 5 outside the optical path onto the optical path.

A self-image generation unit 11 generates an image of the self-image obtained by imaging the self-image of the phase grating 5 based on X-ray detection data the FPD 4 outputs. The image of the self-image is an image on which a striped pattern of the phase grating 5 is reflected. This image of the self-image is sent out to a perspective image generation unit 12. The perspective image generation unit 12 interprets disturbance of the striped pattern on the image of the self-image, and generates a perspective image obtained by imaging phase shift of the X-ray. The perspective image is an image in which the phase shift of the X-ray that differs depending on the place of the subject M is visualized, and indicates the internal structure of the subject M.

Each unit 11, 12, 16, and 18 is implemented by a CPU executing software. Alternatively, each unit 11, 12, 16, and 18 may be implemented by a microcomputer that functions as each unit.

As described above, the present invention can provide the X-ray phase contrast imaging device that can deal with various imaging purposes. That is, the device of the present invention can change the arrangement pitch of the slits S related to the multi-slit 3b and the arrangement pitch of the phase shift sections 5a related to the phase grating 5. The positional relationship among the multi-slit 3b, the phase grating 5, and the FPD 4 is determined based on the arrangement pitch of the slits S related to the multi-slit 3b, the arrangement pitch of the phase shift sections 5a related to the phase grating 5, and the arrangement pitch of the detection elements 4p related to the FPD 4.

According to the present invention, among these arrangement pitches, by changing the arrangement pitch of the slits S and the arrangement pitch of the phase shift sections 5a, the present invention can change the positional relationship among the multi-slit 3b, the phase grating 5, and the FPD 4. When the positional relationship among the multi-slit 3b, the phase grating 5, and the FPD 4 is changed, the enlargement ratio of the self-image of the phase grating 5 reflected on the FPD 4 can be changed. With such a configuration, the present invention can deal with various imaging purposes.

Note that when the arrangement pitch of the slits S and the arrangement pitch of the phase shift sections 5a are changed, it becomes unnecessary to change the arrangement pitch of the detection elements 4p related to the FPD 4 when the enlargement ratio of the self-image is changed. Such a configuration makes it possible to change the enlargement ratio while using the same FPD 4.

The present invention is not limited to the above-described configuration, but can be implemented as modifications as follows.

Figure 17:
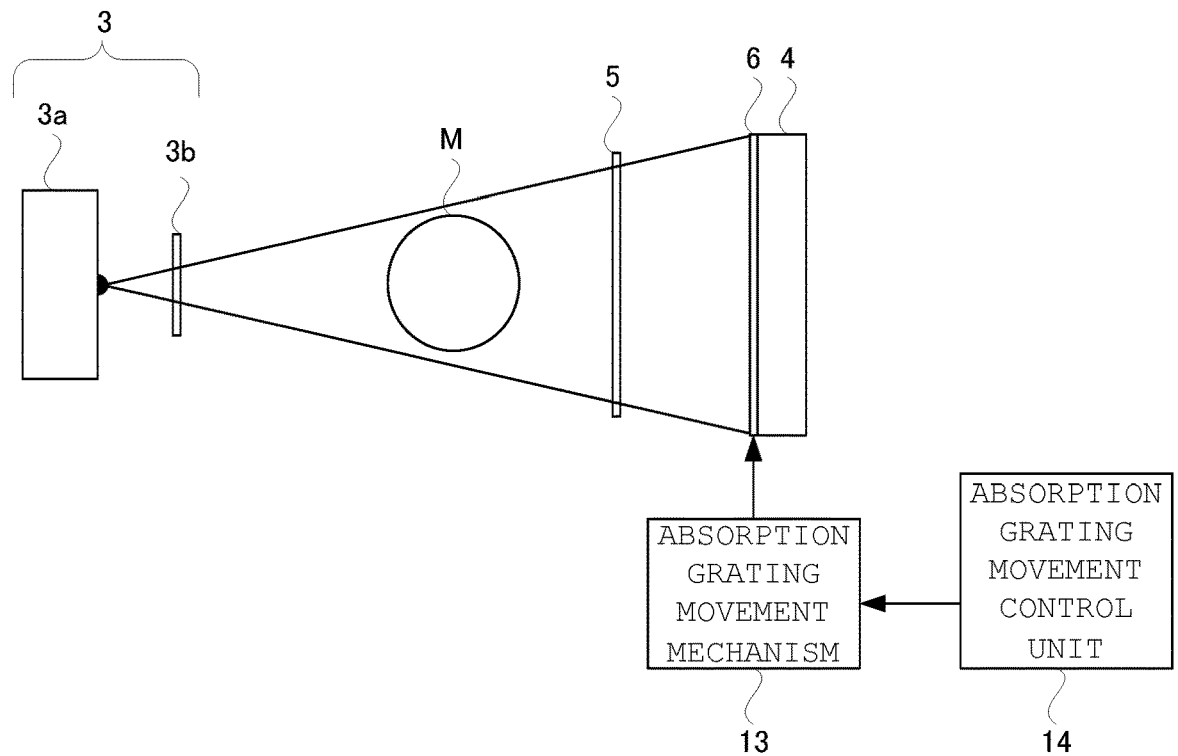
FIG. 17 is a schematic diagram describing one modification of the present invention.
Figure 18:
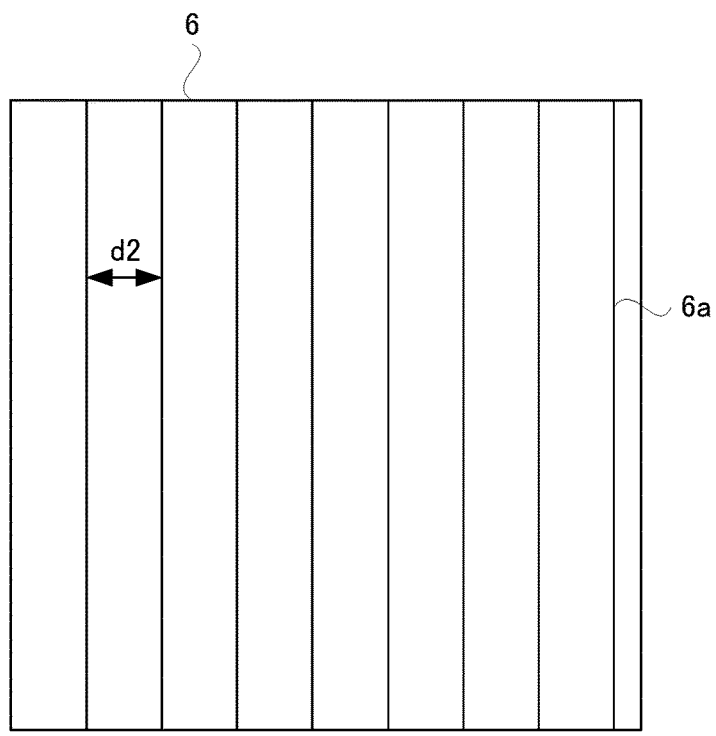
FIG. 18 is a schematic diagram describing one modification of the present invention.

(1) As shown in FIG. 17, the present invention may be applied to a configuration including the absorption grating 6 that covers the detection surface of the FPD 4, an absorption grating movement mechanism 13 that causes the absorption grating 6 to move to the FPD 4, and an absorption grating movement control unit 14 that controls the absorption grating movement mechanism 13. This modification describes a device regarding the fringe scanning method. As shown in FIG. 18, the absorption grating 6 includes elongated phase shift sections 6a that absorb the X-ray arranged at the same pitch as the arrangement pitch d2 of the bright lines of the self-image. A direction in which the absorption grating movement mechanism 13 moves the absorption grating 6 is the arrangement direction of the phase shift sections 6a. With this configuration, the arrangement pitch of the FPD 4 can be wider. A direction in which the slits S in the multi-slit 3b extend agrees with a direction in which the phase shift sections 5a in the phase grating 5 extend and also agrees with a direction in which the phase shift sections 6a in the absorption grating 6 extend.

(2) The present invention is also applicable to a device according to a moire one imaging method. The moire one imaging method is a method for capturing an image in a state where the direction in which the phase shift sections in the absorption grating 6 extend is inclined with respect to the direction in which the phase shift sections in the phase grating 5 extend, and the absorption grating 6 is not moved toward the FPD 4.

(3) The first embodiment has a configuration of including two types of multi-slits 3b, but the present invention may have a configuration of including three or more types of multi-slits 3b. In this case, the multi-slit switching mechanism 15 switches the multi-slits 3b to place one of three or more types of multi-slits 3b on the optical path of the X-ray. This modification implements the change in the arrangement pitch of the slits S by including the plurality of multi-slits 3b different in the arrangement pitch of the slits S, and by the multi-slit switching mechanism 15 switching which multi-slit 3b to transmit the X-ray among the plurality of multi-slits 3b.

(4) The first embodiment has a configuration in which two types of multi-slits 3b are integrated, but the present invention is not limited to this configuration. The present invention may have a configuration of including two types of multi-slits 3b as different bodies. Also, the first embodiment has a configuration of including the separate phase grating 5, but the present invention is not limited to this configuration. The present invention may have a configuration in which two types of phase gratings 5 are integrated. The phase grating switching mechanism 17 according to such a configuration includes a mechanism that slides the phase grating 5 in a direction orthogonal to an emission direction of the X-ray, and a mechanism that moves the phase grating 5 in the emission direction of the X-ray. This allows the phase grating switching mechanism 17 to change a section through which the X-ray passes by sliding the phase grating 5, and to change the distances R1 and R2 described in FIG. 13 and FIG. 14 by moving the phase grating 5.

Figure 19:
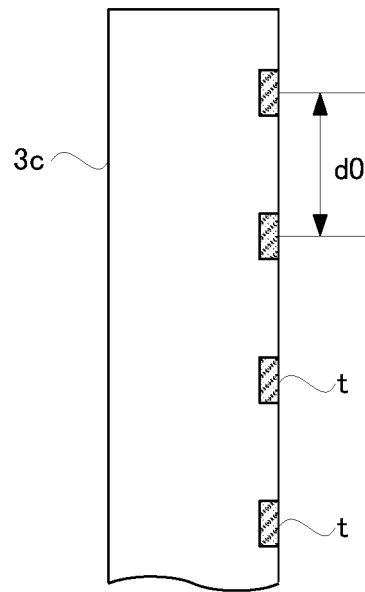
FIG. 19 is a schematic diagram describing one modification of the present invention.

(5) The first embodiment has a configuration of including the multi-slit 3b, but the present invention is not limited to this configuration. The present invention is also applicable to the X-ray phase contrast imaging device having a configuration of not including the multi-slit 3b. The device according to this modification includes a substrate 3c as an X-ray emission source as shown in FIG. 19. Targets t that generate X-rays are arranged at predetermined intervals on the substrate 3c. The targets t are embedded in the substrate 3c, and are configured to emit the X-rays in response to a collision of electrons. When the substrate 3c emits the X-rays, electrons are allowed to collide with the plurality of targets t simultaneously. Then, the X-rays are emitted from respective targets. The emitted X-rays interfere with each other and become a beam with a uniform phase as a whole.

The configuration of the first embodiment makes the phase uniform by causing the X-rays emitted from respective slits S included in the multi-slit 3b to interfere with each other. This modification is configured to make the phase of the X-rays uniform by arranging the targets for emitting the X-rays on the substrate 3c. That is, instead of the multi-slit 3b, the targets generating the X-rays are arranged. The arrangement pitch of the targets t embedded in the substrate 3c of this modification corresponds to the arrangement pitch d0 of the slits S in the multi-slit 3b according to the first embodiment. In this sense, FIG. 19 represents the arrangement pitch of the targets t as d0. Therefore, the arrangement pitch d0 of the targets t needs to satisfy the equation described in FIG. 6.

Figure 20:
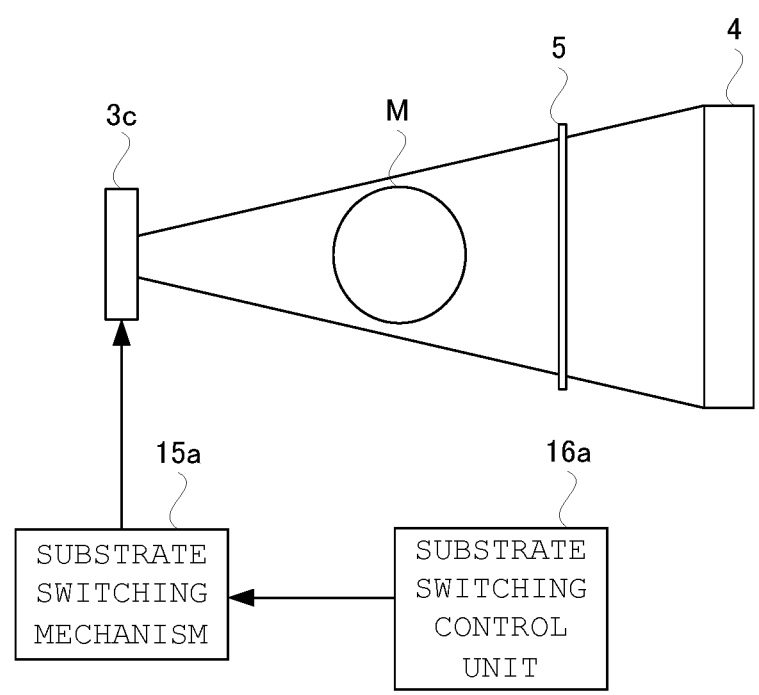
FIG. 20 is a schematic diagram describing one modification of the present invention.
Figure 21:
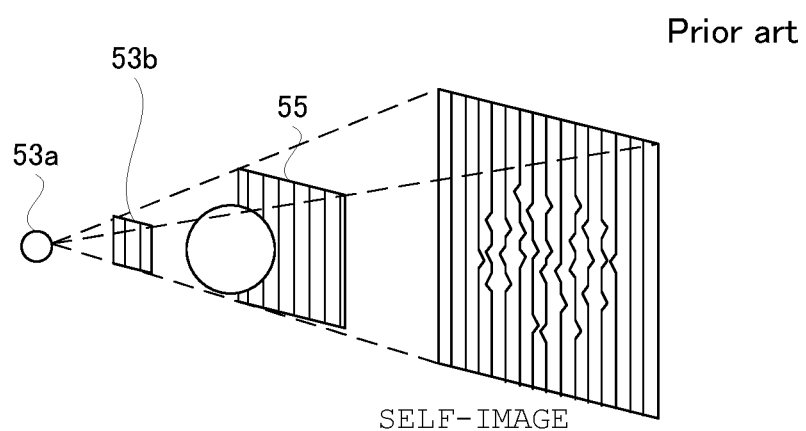
FIG. 21 is a schematic diagram describing a device according to a conventional configuration.

In this modification, a plurality of sections are provided on the substrate 3c. The arrangement pitch d0 of the targets t differs among the sections. The section to emit the X-ray is changed in accordance with the change in the configuration of the phase grating 5 between the mode for low magnification imaging and the mode for high magnification imaging. Such a change in the substrate 3c is performed by a substrate switching mechanism 15a as shown in FIG. 20. A substrate switching control unit 16a is configured to control the substrate switching mechanism 15a. How the substrate switching mechanism 15a slides the substrate 3c in accordance with each mode is similar to the operation of the multi-slit switching mechanism 15, and thus descriptions thereof will be omitted. The substrate switching mechanism 15a corresponds to a target arrangement pitch change unit of the present invention. Note that instead of providing the substrate 3c including the plurality of sections, this modification may include a plurality of substrates 3c different in the arrangement pitch of the targets t.

The present invention is also applicable to a configuration without the multi-slit 3b. The configuration according to this modification includes the plurality of targets t instead of the multi-slit 3b. When the arrangement pitch of the targets t is changed, an effect similar to an effect of changing the arrangement pitch of the slits S in the multi-slit 3b is obtained. Based on this principle, the substrate switching mechanism 15a of this modification is configured to change the arrangement pitch d0 of the targets t that emit the X-rays on the substrate 3c. How the phase grating 5 is changed in accordance with switching of the substrate 3c is similar to the first embodiment.

(6) Note that the above-described embodiment and the modifications have described the device configuration including the two modes different in the enlargement ratio of the self-image, but the present invention is not limited to this configuration. The device according to the present invention may have a configuration including three or more modes different in the enlargement ratio of the self-image. The multi-slit 3b according to this modification may have the number of sections different in the arrangement pitch of the slits S according to each mode, and may include the plurality of multi-slits 3b different in the arrangement pitch of the slits S. Alternatively, the device according to the present invention may have a configuration including the plurality of sections different in the arrangement pitch of the targets t on the substrate 3c according to each mode. Also, the device according to the present invention may have a configuration including the plurality of substrates 3c different in the arrangement pitch of the targets t.

Similarly, this modification may have a configuration including the number of phase gratings 5 different in the arrangement pitch of the phase shift sections according to each mode. In this case, the phase grating switching mechanism 17 switches the phase grating 5 such that one of the three or more types of phase gratings 5 is placed at a different position on the optical path of the X-ray.

(7) The above-described configuration is a device using the phase grating 5, but the present invention is not limited to this configuration. The absorption grating 5 may be used instead of the phase grating 5. In the absorption grating 5, linear X-ray absorption sections that absorb the X-rays are arranged at predetermined intervals. When the X-ray enters the X-ray absorption sections of the absorption grating 5, the X-ray is absorbed there. Also, the X-ray can pass between the X-ray absorption sections adjacent to each other. With the device using such an absorption grating 5, the striped pattern is formed on the FPD 4, but this striped pattern is not the self-image but a shadow of the absorption grating 5. Also, instead of the FPD detecting the self-image of the phase grating, the shadow generated by absorption by the phase grating may be detected.

REFERENCE SIGNS LIST

3a X-ray source (radiation source)
3b multi-slit
4 FPD (detector)
5 phase grating (grating)
15 multi-slit switching mechanism (slit arrangement pitch change unit)
15a substrate switching mechanism (target arrangement pitch change unit)
17 phase grating switching mechanism (grating change unit)

The invention claimed is:

1. A radiation phase contrast imaging device comprising:
a radiation source configured to emit a radiation;
a multi-slit including a plurality of slits arranged to transmit the radiation generated from the radiation source;
a grating including linear structures arranged;
a detector configured to detect a self-image of the grating or a shadow produced through absorption by the grating, the detector including detection elements arranged longitudinally and latitudinally, the detection elements detecting the radiation;
a slit arrangement pitch change unit configured to change an arrangement pitch of the slits related to the multi-slit at a position through which the radiation emitted from the radiation source passes; and
a grating change unit configured to change an arrangement pitch of the structures related to the grating and a distance between the grating and the detector when the arrangement pitch of the slits is changed.

2. The radiation phase contrast imaging device according to claim 1, wherein
the multi-slit includes a plurality of portions different in the arrangement pitch of the slits, and
the slit arrangement pitch change unit implements change in the arrangement pitch of the slits by moving the multi-slit relative to the radiation source.

3. The radiation phase contrast imaging device according to claim 1,
further comprising a plurality of the multi-slits different in the arrangement pitch of the slits,
wherein the slit arrangement pitch change unit implements change in the arrangement pitch of the slits by switching which of the plurality of the multi-slits to transmit the radiation.

4. The radiation phase contrast imaging device according to claim 1, wherein
the grating includes a plurality of portions different in the arrangement pitch of the structures, and
a structure arrangement pitch change unit implements change in the arrangement pitch of the structures by moving the grating relative to the radiation source.

5. The radiation phase contrast imaging device according to claim 1, further comprising a plurality of the gratings different in the arrangement pitch of the structures,
wherein a structure arrangement pitch change unit implements change in the arrangement pitch of the structures by switching which of the plurality of the gratings to transmit the radiation.

6. The radiation phase contrast imaging device according to claim 1, further comprising an absorption grating placed on a side of the radiation source from the detector,
wherein imaging of a phase contrast is performed by a fringe scanning method or moire one imaging method.

7. A radiation phase contrast imaging device comprising:
a radiation source configured to make a phase of radiations uniform by arrangement of targets that emit the radiations;
a grating including linear structures arranged;
a detector configured to detect a self-image of the grating or a shadow produced through absorption by the grating, the detector including detection elements arranged longitudinally and latitudinally, the detection elements detecting the radiation;
a target pitch change unit configured to change an arrangement pitch of the targets that emit the radiations in the radiation source; and
a grating change unit configured to change an arrangement pitch of the structures related to the grating and a distance between the grating and the detector when the arrangement pitch of the targets is changed.

* * * * *